United States Patent [19]

Beach

[11] Patent Number: 5,102,626
[45] Date of Patent: Apr. 7, 1992

[54] MATRIX MODIFIER FOR MODIFYING A MATRIX TO IMPROVE ANALYSIS OF METAL CONSTITUENTS DURING GRAPHITE FURNACE ATOMIC ABSORPTION SPECTROSCOPY

[75] Inventor: Lucinda M. Beach, Glendale Heights, Ill.

[73] Assignee: Varian Associates, Inc., Palo Alto, Calif.

[21] Appl. No.: 258,487

[22] Filed: Oct. 17, 1988

Related U.S. Application Data

[62] Division of Ser. No. 22,966, Mar. 6, 1987, Pat. No. 4,806,489.

[51] Int. Cl.$^5$ .............................................. G01J 3/42
[52] U.S. Cl. .................................... 422/99; 436/155; 436/159; 436/171; 436/182; 356/312
[58] Field of Search ............... 436/155, 159, 171, 182; 356/312; 422/99

[56] References Cited

U.S. PATENT DOCUMENTS

4,795,618  1/1989  Laumen ............................. 422/312
4,902,535  2/1990  Garg et al. ......................... 427/249

Primary Examiner—David L. Lacey
Assistant Examiner—Abanti B. Singla
Attorney, Agent, or Firm—Stanley Z. Cole; Gerald M. Fisher; Edward H. Berkowitz

[57] ABSTRACT

A matrix modifier of finely-divided metallic palladium dispersed to contact a metal constituent to improve analysis of the constituent during graphite furnace atomic absorption spectroscopy. The palladium interacts with a variety of metals in a sample to increase the vaporization temperatures of the metals. One way of contacting palladium with the metal analyte is to introduce it as a salt in solution with the sample into the graphite furnace along with a surfactant. A finely-divided metallic palladium having high surface area is produced in the furnace by introduction of hydrogen gas, which acts as a reducing agent, to reduce and maintain palladium in its metallic form at an early point in the temperature program, prior to evaporation of the surfactant.

3 Claims, 7 Drawing Sheets

MATRIX MODIFIER FOR MODIFYING A MATRIX TO IMPROVE ANALYSIS OF METAL CONSTITUENTS DURING GRAPHITE FURNACE ATOMIC ABSORPTION SPECTROSCOPY

RELATED APPLICATION

The present patent application is a division of Ser. No. 022,966, filed Mar. 6, 1987, now U.S. Pat. No. 4,806,489.

BACKGROUND OF THE INVENTION

Generally, the invention relates to an apparatus and a method for graphite furnace atomic absorption spectroscopy. In particular, the invention relates to matrix modifiers for graphite furnace atomic absorption spectroscopy which improve quantitative measurement of metal constituents in unknown samples.

Although there are different approaches to the detailed design and construction of furnace atomizers, all perform the same fundamental process—to generate a population of free analyte atoms so atomic absorption can be measured. In its simplest form, this process is achieved in three stages of heating of the furnace:

1. The drying stage to remove solvent from the sample;
2. An ashing stage to remove organic molecules or inorganic materials; and
3. The atomization stage to generate free analyte atoms within a confined zone coincident with the spectrophotometers optical path.

It is very desirable to produce a well-defined peak of optical absorption during the atomization stage. The height and area of this peak is related to the amount of analyte present in the sample and the conversion efficiency of the atomization. Peak characteristics are presented on a chart recorder or established by electronic peak measurement systems built directly into the spectrophotometer. Such systems typically provide both height and area measurements from one characteristic peak. Concentration values of metal analytes are calculated for unknown samples using comparative measurements with predetermined standards containing those metal constituents.

Theoretically, conversion efficiency of the analyte in the sample into vaporized free metallic molecules whose light absorption is measured by the spectrophotometer should be high because all the available sample is used to produce the atom population within the optical path, i.e. the metal atoms are all vaporized and, if they cross the optical path, measured by the spectrophotometer. However, the conversion efficiency is disrupted by two primary causes:

1. Loss of the analyte as a molecule, usually in combination with oxygen or chlorine, at a temperature below the vaporization temperature of the free metal analyte; and
2. Interference at the higher vaporization temperature of the analyte from molecules not containing the analyte, but absorbing in the measured range.

In the past, attempts were made to reduce interference by modifying the chemical matrix of the sample to be tested. Typically, a substituent was added to the solution containing the sample to stabilize the analyte, keeping it from being vaporized as an oxygen, chloride or other salt at a temperature below the vaporization, i.e. dissociation, step in the graphite furnace atomic absorption spectroscope procedure.

A poster session was presented on this topic in September, 1985, in Germany, for the P.R.O.C. Coll. Spec. Int. XXIV, Paper Tue. 077, by G. Schlemmer and B. Welz. In this work palladium and other platinum group elements were shown to stabilizing effect during graphite furnace atomic absorption spectroscopy on the metal analytes of arsenic, tellurium, mercury, thallium, lead and gold. The paper concludes that a mixture of palladium nitrate and magnesium nitrate can be used as a modifier for the more volatile elements of periodic groups IIIA to VIA of the periodic system. An increase in the vaporization temperature of several analytes is achieved and the risk of vapor phase interference is reduced accordingly.

Grobinski, Erler and Voellkopf authored an article entitled "Determination of Mercury With Zeeman Graphite Furnace AAS", appearing in Atomic Spectroscopy, Vol. 6, No. 4, July-August, 1985, which identified palladium as a matrix modifier for use in measuring mercury. The authors speculated that because palladium worked successfully as a matrix modifier only when pre-treated at 1000° C. to 1100° C., metallic palladium is formed at this high temperature and a stable compound is thereafter formed with the mercury though "amalgation". However, since gold and platinum do not work similarly to modify the matrix, they further concluded that simple amalgation is not the reason for the resulting matrix modification. The authors speculated that because palladium forms an oxide more readily than gold or platinum, such an oxide may be somehow required or involved in the reaction.

Palladium and ascorbic acid together have been shown to prevent interference normally present from perchloric acid in geological samples of river sediments tested for the presence of indium. Shan Xiao-Quan, Ni Zhe-Ming and Yuan Zhi-Neng wrote an article entitled "Determination of Indium in Minerals, River Sediments and Coal Fly Ash by Electrothermal Atomic Absorption Spectrometry With Palladium as a Matrix Modifier", *Analytica Chemica Acta*, 171, pp. 269-77, 1985, discussing this. Ascorbic acid and palladium are both disclosed as matrix modifiers for analyzing indium.

Although palladium has been known as a successful matrix modifier in the prior art, particularly for indium, thallium, tin, lead, arsenic, antimony, bismuth, selenium and tellurium in control samples, such disclosed methods are less valuable in testing true unknown samples where chemical interference cannot be standardized. Each constituent added as a solution in the graphite furnace contributes further contamination or, at least, the potential for contamination. When complex interactions, often times not fully understood even in controlled tests, are occurring in an unknown sample tested for a given analyte, such contaminants can effect the results by chemically interacting with the metallic analyte, or spectroscopically interfering by forming complexes which will absorb at the characteristic wavelength of the analyte in the vaporization temperature range of the analyte. Even the addition of reducing reagents in solution such as ascorbic acid, disclosed in the Shan Xiao-Quan article discussed above, introduce yet additional unknown constituents to the sample to be tested. Because of its reducing characteristics, ascorbic acid would have to be added as a separate solution in addition to the palladium in solution. Ascorbic acid is a powerful reducing agent and will precipitate palladium out of solution rapidly, making a pre-mixed solution impractical.

The Grobinski et al.'s method of reducing palladium at high temperatures, 1000° C. to 1100° C., is not practical because it requires a pre-heating step wherein the palladium is reduced by the hot graphite and cooled in the furnace before the sample is added to the furnace and the three-stage temperature scheme run. This is contrary to normal testing procedure and significantly increases the time needed for each analysis.

It is an object of the present invention to provide a matrix modifier which can be used to modify any of a large number of metal analytes in unknown samples without introducing additional contamination of a reducing agent in solution. It is another object of the present invention to provide a matrix modifier which can be used in unknown samples to test for a broad range of metal analytes and to improve the quantitative results of those tests. It is another object of the present invention to provide a matrix modifier which allows for a significant increase in the ash phase temperature but does not require a separate pretreatment step of the palladium, and which can be used to test a wide range of metallic analytes in unknown samples. It is yet another object to provide a method of modifying the matrix of a sample to increase the vaporization temperature of a metal analyte contained therein. It is yet an additional object of the present invention to provide a form of reduced palladium in the graphite furnace in contact with the metal analyte to obtain optimum effect of the palladium matrix modification properties. It is yet a further object of the present invention to provide an apparatus and method in which palladium is presented in an efficient form to metal constituents in unknown and known samples without contributing contamination of a reducing agent in solution. Further and additional objects will become apparent from the following discussion of the invention and its various embodiments.

SUMMARY OF THE INVENTION

The present invention contemplates a matrix modifier, a method for modifying a matrix, and an improved graphite furnace, which provide palladium in a very effective form to metal analytes contained in samples in a graphite furnace to improve analysis of those analytes during atomic absorption spectrophotometry. Further, the use of a gas as a reducing agent lessens the contamination contributed by a reducing agent in solution. The invention provides palladium as a matrix modifier in a practical form that can be used for many metallic analytes in many kinds of unknown samples.

Research into the matrix modifying properties of reduced palladium led to the surprising and unobvious discovery that the form of palladium presented to metal constituents is crucial to achieving the desired matrix modification. A surface of finely-divided palladium particles having average diameters less than about 0.10 microns, presenting a high surface area, dispersed on the graphite furnace (or the solid residue left by evaporation of solvents in the sample solution) will interact with metal constituents to decrease their oxidation or chlorination at lower temperatures in the graphite furnace and increase their vaporization or dissociation temperatures by several hundred degrees. Palladium now can be broadly exploited as a matrix modifier for transition elements, and elements in groups III, IV, V and VI of the periodic table.

The invention is achieved in one form by introducing a solution containing the sample and palladium into the graphite furnace and introducing a reducing gas into the graphite furnace to reduce the palladium to its metallic state. Also contemplated is a method of increasing the vaporization temperatures of metallic constituents of a sample in a graphite furnace by contacting the metallic constituent with particles of finely-divided palladium dispersed in the graphite furnace, improved dispersion achieved by the addition of a surfactant. Also, as part of the present invention, an improved graphite furnace for increasing the vaporization temperatures of metal constituents and samples during atomic absorption spectroscopy achieves the improvement by having the interior wall of the graphite furnace contain, on at least a portion of its surface, finely-divided metallic palladium particles, whereby metal constituents contact the palladium during the temperature sequence leading to vaporization of the constituent.

BRIEF DESCRIPTION OF THE DRAWINGS

FIG. 4b shows a 20,000 X magnification electron microscope photograph of palladium photographed in FIG. 4a.

DETAILED DESCRIPTION OF THE INVENTION

Figure 1:
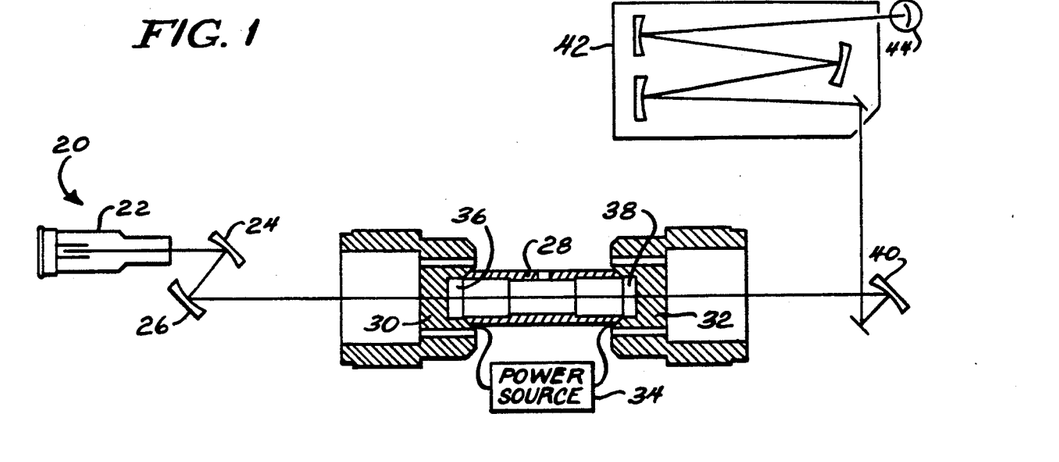
FIG. 1 is a schematic drawing of a graphite furnace atomic absorption spectophotometer.

The present invention has many different applications. A simple schematic representation of a graphite furnace atomic absorption spectrophotometer is shown in FIG. 1 generally as 20. A hollow cathode lamp 22 emits a beam of light having wavelength corresponding to the characteristic absorption of the metallic analyte which is desired to be quantified. For example, lead has characteristic absorption wavelengths of 217.0 nanometers and 283.3 nanometers. Of course, most spectrophotometers allow for substitution of cathode lamps so that many different metallic analytes can be studied at their characteristic wavelengths in a single spectrophotometer.

A first mirror 24 and second mirror 26 deflect the beam of light so that it will pass through, and be surrounded by, the graphite furnace or tube 28 and associated mechanisms described below. The graphite furnace is held by two electrodes 30 and 32 connected to opposite poles of a power source 34 so a current having large amperage and low voltage can be drawn across the graphite tube 28, which thereby acts as a heater. As is known in the art, the temperature of the graphite tube can be increased very rapidly from room temperature to about 3000° C. using this method. Port windows 36 and 38 allow light to pass through the ends of the mechanism but do not allow gasses present in the graphite tube to escape through its ends.

After passing through the graphite tube and associated apparatus the light is reflected by a third mirror 40 and into a monochromator 42 which isolates the characteristic wavelength of each element to be studied. Detector 44 measures the amount of light attenuated at the characteristic wavelength which, theoretically, is the amount of light absorbed by the analyte in the gas which crosses the optical path.

Figure 2:
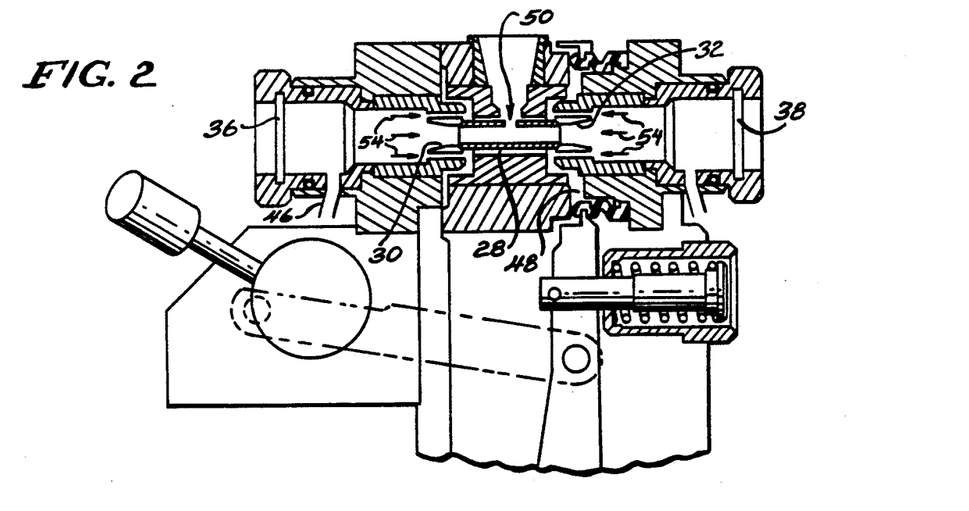
FIG. 2 is a detailed schematic representation of the graphite furnace itself and associated mechanisms.

FIG. 2 shows details of a graphite furnace mechanism including port windows 36 and 38, graphite tube 28 and electrodes 30 and 32. This detailed view however shows gas entry portholes 46 and 48 and sample injection port 50 which also provides for venting of gas.

The samples are placed in the tube through the sample injection port 50 to rest inside the graphite tube 28. It should be noted that the sample which has entered through the injection port may be either a control or an unknown, but usually it will be in liquid form such as a solution to be tested for the presence and concentration of a specific metallic analyte. Such a liquid will rest on the bottom of the graphite tube and eventually will be dried during the heating steps to a solid, granular, or powder state.

Oxidation of the same by oxygen present in the air at increased temperatures is greatly reduced or eliminated by flowing inert gas such as argon or nitrogen through the graphite tube during the ash temperature stage, as is shown by arrows 54. Normally, however, the flow of the gas through the graphite tube is discontinued just prior to temperatures which will dissociate the analyte to avoid blowing the analyte out of the injection port 50 too quickly. That is, the metallic analyte is desired to be maintained in a gaseous state inside the graphite tube, in the optical path, as long as possible to maximize sensitivity of the reading of the spectrophotometer.

Figure 3A:
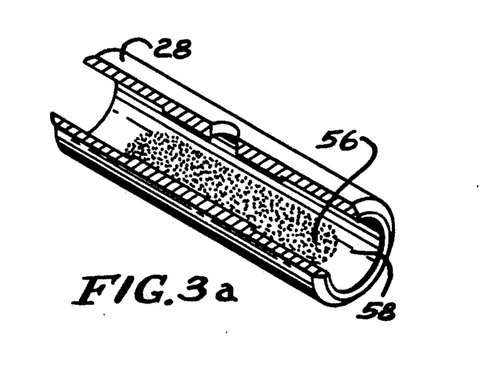
FIG. 3a is a detailed perspective of the graphite furnace contemplated by the present invention, shown cutaway.
Figure 3B:
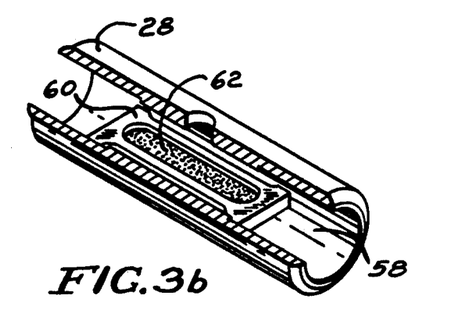
FIG. 3b is a detailed perspective of the graphite furnace and platform contemplated by the present invention, the furnace shown cut-away to reveal the internal contents.

FIGS. 3a and 3b show details of an embodiment of a graphite tube 28 contemplated by the present invention which has internal coating of finely-divided dispersed metallic palladium 56 on its internal surface 58 to be in contact with the sample solution which is injected through the injection port and which sits in the bottom of the graphite tube. Alternatively, graphite platform 60, shown in FIG. 3b, can be used to present a temperature delay or lag time wherein the gaseous environment inside the graphite tube heats up at a faster rate than the solution on the platform. The platform has holding indentation 62 to contain the sample. Finely-divided, dispersed palladium can be present on the surface of the platform at the indentation. This can be achieved in several ways as will be discussed below.

Improved results are obtained by use of the present invention to contact a finely-divided, dispersed metallic palladium having high surface area with metallic constituents in the sample which will be measured by atomic absorption spectroscopy when vaporized in a graphite furnace. Preferably, a solution of a palladium salt, such as palladium chloride or palladium nitrate in a dilute nitric acid/hydrochloric acid solution is mixed with the sample, either a control or an unknown, and the resulting solution is injected through the sample injection port into the graphite tube where it will rest on the bottom of the graphite tube, or on the indentation 62 of the platform 60.

Normally, the hot graphite in contact with the palladium in solution will reduce the palladium to the reduced metallic state at about 400°–600° C. The electron microphotographs in FIGS. 4a and 4b show the large globuals of palladium, many stuck to each other in even larger globuals, but at best showing cylindrical clumps.

Figure 4A:
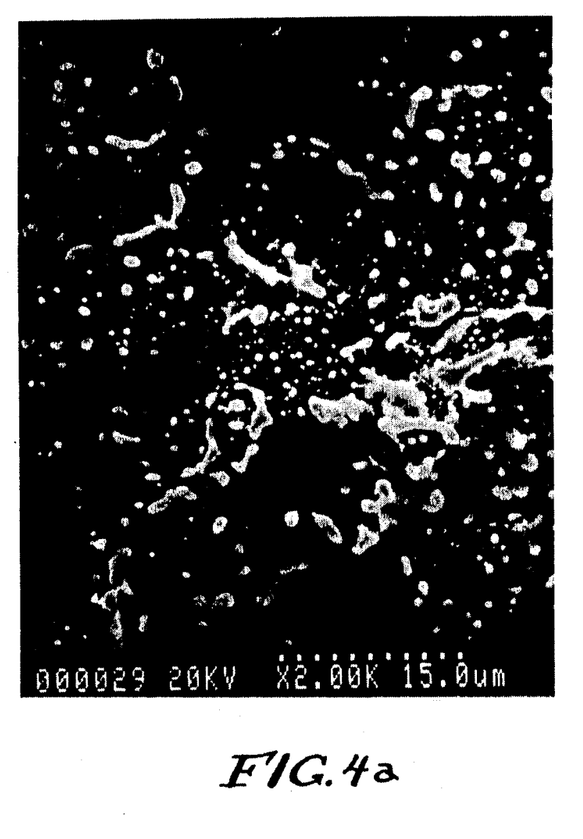
FIG. 4a shows a 2000 X magnification electron microscope photograph of palladium deposited with hydroxylamine HCl on pyrolytic graphite, wherein the graphite was heated to 1000° C.
Figure 4B:
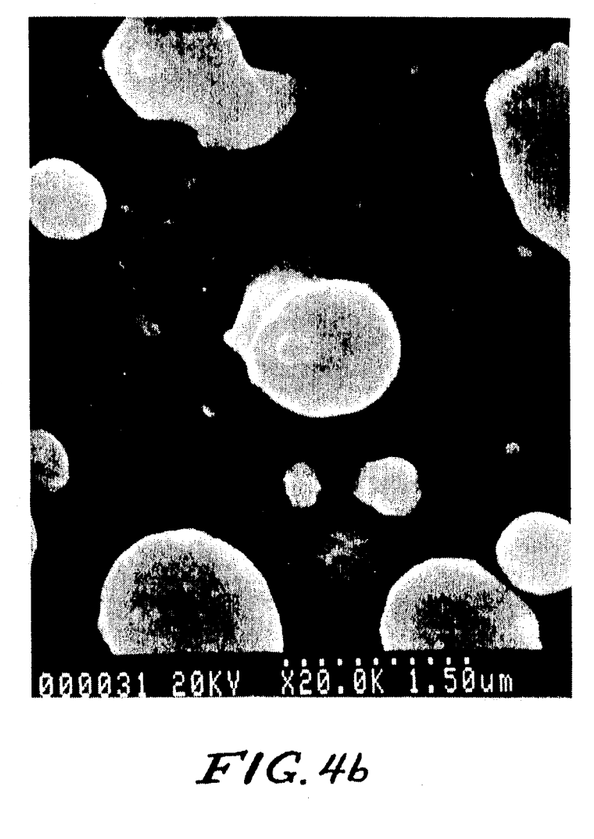

The palladium shown in FIGS. 4a and 4b was obtained from a palladium/hydroxylamine HCl mixture, the palladium being reduced by the hot graphite furnace and the hydroxylamine HCl. As indicated in the micrographs, there is considerable variation in palladium particle size. Some of the palladium globuals are several microns in diameter. A portion of the same surface at 20,000 X magnification, shown in FIG. 4b, clearly illustrates palladium droplets approximately 1 micron in diameter (scale is indicated at the bottom of each micrograph). Although hydroxylamine HCl was used here, however, pre injecting a palladium solution with no reducing agent and heating to 1000° C. produced a very similar type of distribution of palladium.

Figure 5A:
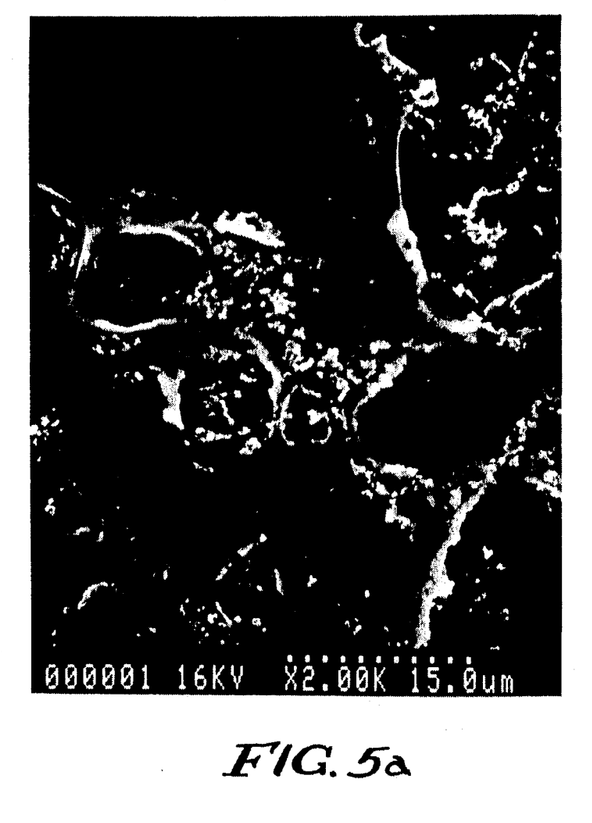
FIG. 5a is a 2000 X magnification electron microscope photograph of palladium deposited with ascorbic acid on pyrolytic graphite, the graphite heated to 1000° C.
Figure 5B:
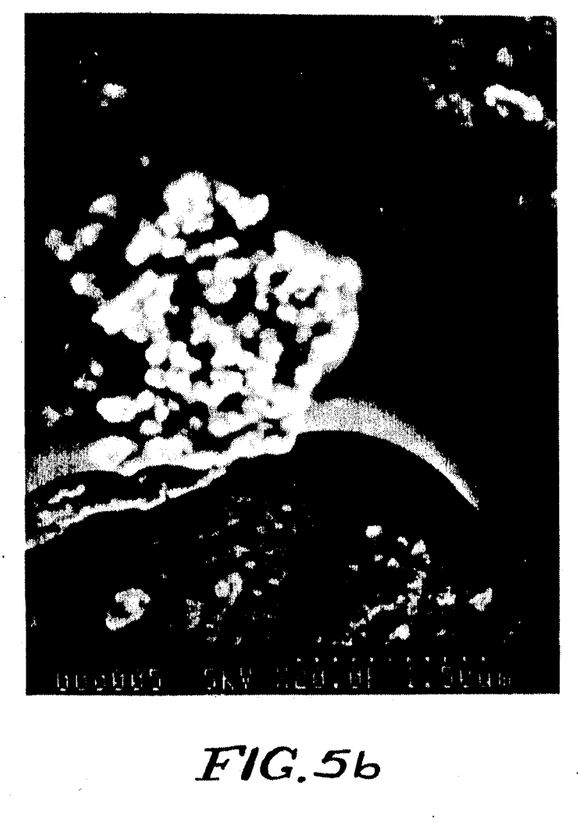
FIG. 5b shows the same palladium as shown in FIG. 5a at 20,000 X magnification.

FIGS. 5a and 5b represent an attempt to reduce the palladium with ascorbic acid. The ascorbic acid appears on the electron micrographs as a webbed structure having clusters of clumped together particles of palladium at certain points. These clusters, themselves larger than the palladium globuals shown in FIGS. 4a and 4b, begin to show formation of much smaller particles. However, the great majority of palladium still exists in these large clumps of palladium metal.

A 2000 X magnification of the deposit on the graphite surface when palladium was introduced with ascorbic acid is shown in FIG. 5a. The palladium particles of lighter intensity appear to be embedded in the carbon residue from the ascorbic acid. Ascorbic acid will precipitate palladium out of solution relatively rapidly, and palladium is probably present as the metal before the solution completely drys. Shown in FIG. 5b is a 20,000 X magnification of a cluster of palladium particles. The darker carbon residue from the ascorbic acid is visible. Apparently when ascorbic acid is used as the reducing agent, relatively small particles of palladium are obtained, however, they are not evenly distributed but are clumped together. In general, ascorbic acid produces better atomic absorption results than hydroxlyamine HCl.

Figure 6A:
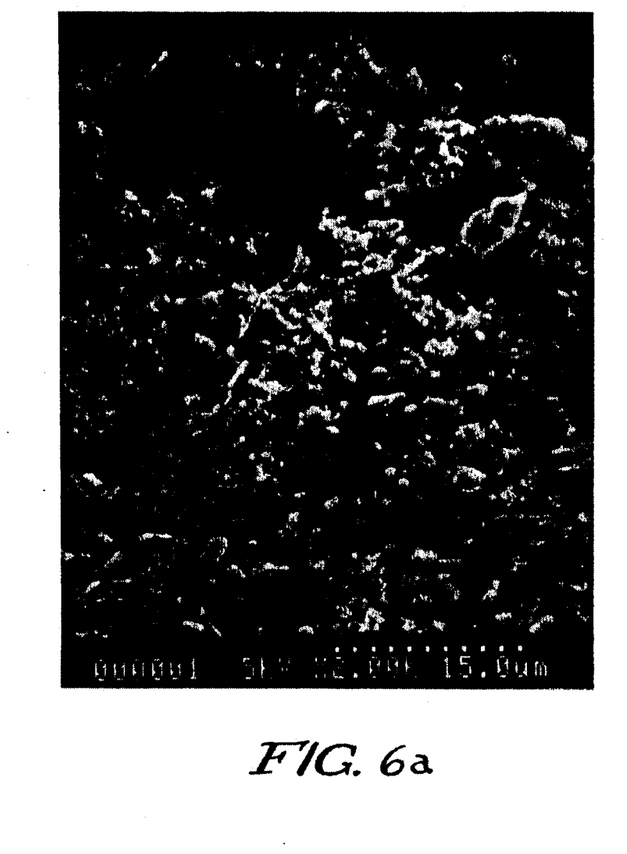
FIG. 6a shows palladium solution dried and reduced with 5 percent hydrogen gas in 95 percent argon gas, with the graphite heated to 1000° C., at 2000 X magnification.
Figure 6B:
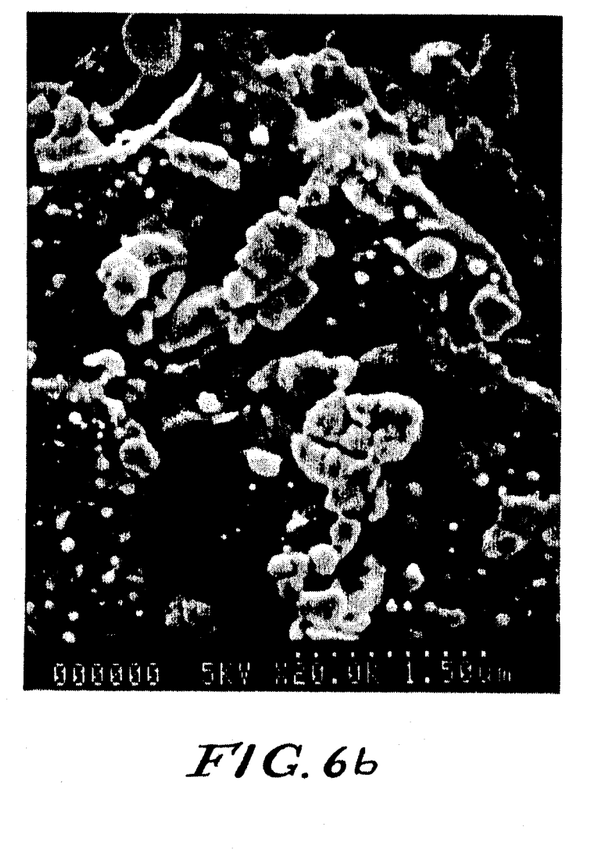
FIG. 6b shows the same palladium of FIG. 6a at 20,000 X magnification.

As was discussed above, the use of hydrogen gas is desired to avoid contamination introduced by a reducing agent in solution, such as ascorbic acid. Hydrogen gas appears to be an effective reducing agent in the graphite furnace and normally will reduce the palladium at below 300° C. As well as early and efficient reduction of the palladium salt to palladium metal, hydrogen may provide other important beneficial effects. The presence of hydrogen in the furnace is known to effect chemical reactions in the gas phase. Its presence promotes the removal of halides and potentially results in reduced partial pressure of oxygen. This improves the efficiency of atom formation by minimizing loss of the analyte atom as a molecule in combination with oxygen or chlorine. Palladium is known to have a very high ability to absorb hydrogen and this possibly results in the catalytic hydrogenation of the graphite surface. This could also effect reactions in the graphite furnace. Electron microscope photographs shown in FIGS. 6a and 6b show palladium reduced with 5 percent hydrogen gas in 95 percent argon and the palladium/graphite surface heated to 1000° C. Metallic palladium appears in dispersed particles, more finely-divided and dispersed than FIGS. 4a, 4b, 5a and 5b, but still showing coagulated clusters of palladium.

Figure 7A:
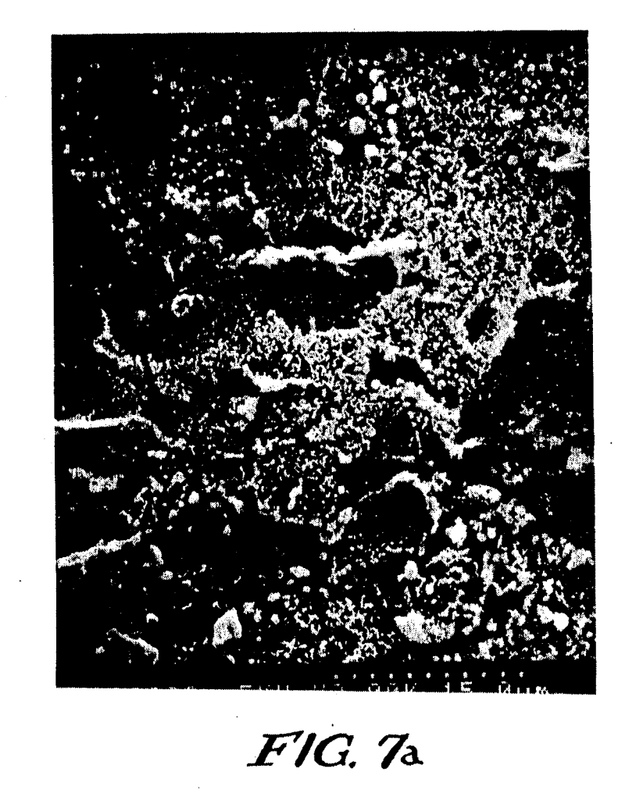
FIG. 7a shows palladium solution containing 1 percent glycerol dried and reduced with 5 percent hydrogen in 95 percent argon, wherein the graphite is heated to 1000° C., at 2000 X magnification.
Figure 7B:
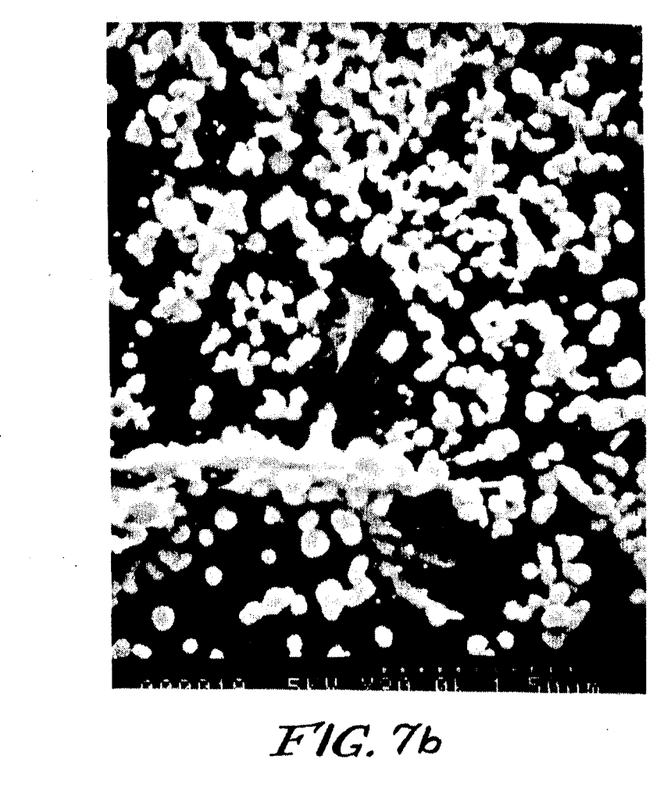
FIG. 7b shows the palladium of FIG. 7a at 20,000 X magnification.

Striking results are displayed in electron microscope photographs 7a and 7b. The palladium in these micrographs was produced by adding 1 percent glycerol in a palladium salt solution, the palladium being reduced thereafter by a 5 percent hydrogen and 95 percent argon atmosphere before heating the graphite furnace to 1000° C. The resulting palladium appears as finely-divided, dispersed particles sprinkled over the graphite surface. Although there are some larger particles of palladium, glycerol has had a pronounced effect on palladium particle size and distribution. The particles are considerably smaller and better dispersed than those seen earlier. An average particle diameter is approximately 0.05–0.15 um. In the upper portion of this micrograph the palladium particles appear to be piled on top of each other without coalesing into a larger droplet This method of introducing palladium with a surfactant and reducing the palladium with hydrogen gave superior atomic absorption when compared to earlier work. Atomization peaks were much better shaped, appearing sharper and more gaussian. The conclusion: smaller, better dispersed particles of palladium produce a great increase in surface area of palladium, thereby producing a superior matrix modification effect.

Figure 8:
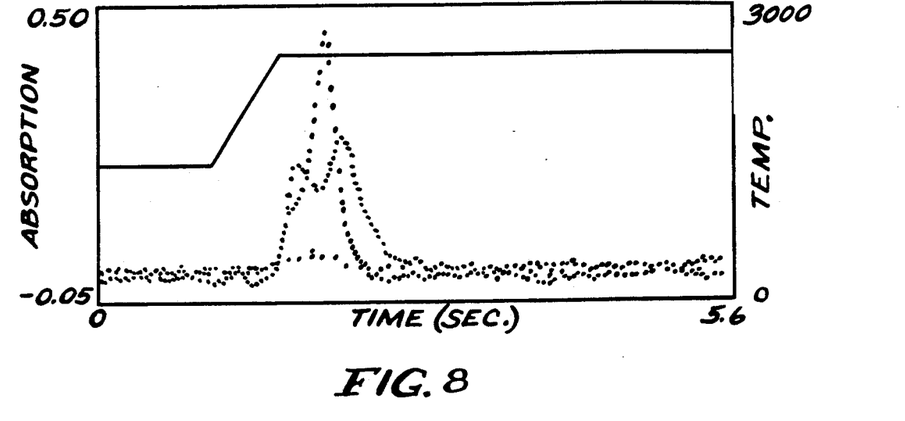
FIG. 8 shows a graphic comparison of two absorption profiles using a palladium/$H_2$ gas matrix modifier, one with 0.5% glycerol surfactant and one without.
Figure 9:
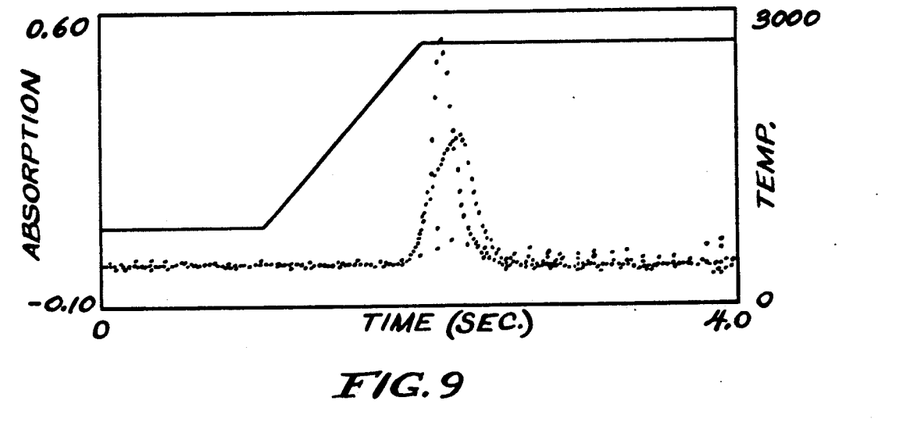
FIG. 9 shows a graphic comparison of two absorption profiles for tin using a palladium/$H_2$ gas matrix modifier, one with 1% glycerol surfactant and one without.

FIGS. 8 and 9 show comparative graphic overlays illustrating the improved absorption characteristics obtained by glycerol added to the palladium/$H_2$ matrix modifier. The graphs in FIG. 8 show modification of a sample containing metal analyte arsenic. The double peaked profile is the absorption of the sample with matrix modified by palladium and $H_2$ gas only, i.e., no glycerol is included. An improved singlepeak absorption is shown which was obtained by matrix modification by palladium/$H_2$ gas and glycerol. The horizontal line near the upper half of the graph indicates the temperature of the furnace.

FIG. 9 similarly shows comparative graphs of matrix modification of tin, the higher peak being obtained by matrix modification with palladium/$H_2$ gas and glycerol surfactant. The less-defined, lower peaked curve is produced by matrix modification with only palladium and $H_2$ gas, without glycerol. It should be noted that the temperature shift effect of the palladium/$H_2$ gas matrix modifier is not improved by the glycerol, but the peak height and definition is significantly enhanced.

It appears that the finely-divided dispersed palladium particles, as shown in FIG. 7, is more effective because of the great increase in surface area presented to the metal analyte. Surface area is a square function of diameter, so a much greater number of smaller diameter spheres of palladium per mass of palladium presents a much more pronounced matrix modification effect.

The electron micrographs of FIGS. 4, 5, 6 and 7 were obtained by using a spectrAA-40 atomic absorption spectrophotometer and GTA-96 graphite tube atomizer with sample dispenser. Manufacturers' standard recommendations for wavelength, SBW and lamp current parameters were followed. The graphite furnace temperature parameters were optimized for individual elements. The equipment was made by Varian Instrument Group, Palo Alto, Calif. The scanning electron micrographs were attained with a Hitachi S-800 Field Emission Scanning Electron Microscope.

Palladium modifier solutions were prepared by dissolving palladium foil (Aldridge Chemical Company, Milwaukee, Wis.) in a minimum volume of aqua regia and diluting with deonized water. Analytical reagent grade hydroxylamine HCl (J. T. Baker Chemical Company, Phillipsburg, N.J.), ascorbic acid and glycerol (Mallinckrodt, Inc. Paris, Ky.) were used to prepare modifier solutions.

Solid pyrolytic platforms were used to obtain palladium surfaces for the scanning electron micrographs. The modifier solutions were deposited onto the platform and the platform was then heated in the graphite furnace to a 1000° C. and held at that temperature for 15 seconds. Four palladium surfaces were prepared.

1. 50 ug Pd, 500 ug hydroxylamine Hcl;
2. 50 ug Pd, 250 ug ascorbic acid (added from separate solutions);
3. 50 ug Pd., solution dried and then reduced with 5 percent hydrogen in 95 percent argon; and
4. 50 ug Pd, 350 ug glycerol, solution dried and then reduced with 5 percent hydrogen in 95 percent argon.

The amounts of palladium and other reagents used to obtain these surfaces were 2-5 times greater than the amounts typically used for chemical modification in an analytical method. This increase was to ensure that the palladium was easily visible by scanning electron microscopy.

Figure 10:
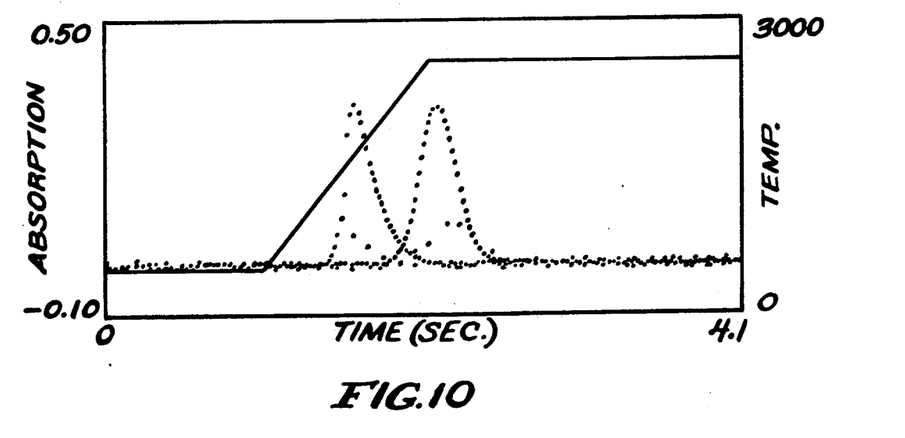
FIG. 10 is a graphic comparison of the absorption of two samples containing lead, one sample also containing a palladium/hydrogen gas/glycerol matrix modifier according to the present invention.
Figure 11:
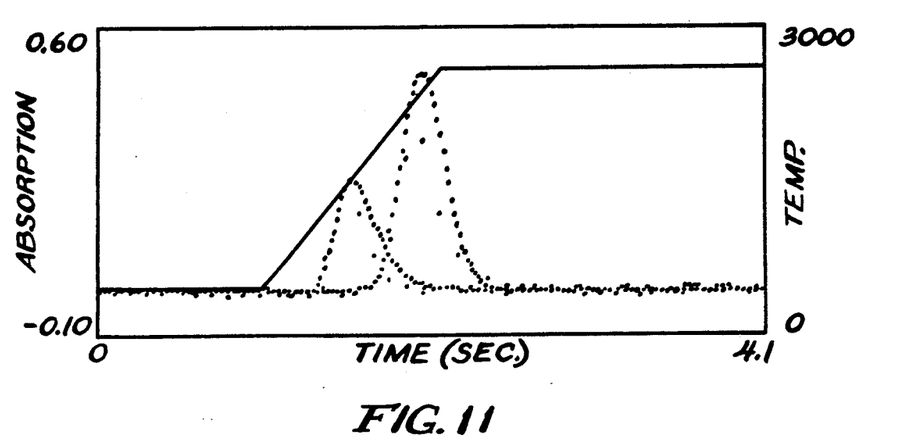
FIG. 11 is a graphic comparison of absorption of two samples containing thallium, one sample also containing a palladium/hydrogen gas/glycerol matrix modifier according to the present invention.
Figure 12:
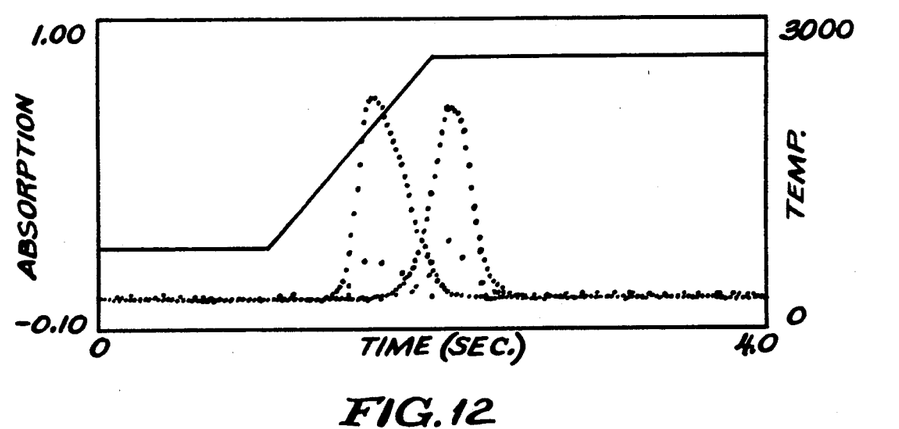
FIG. 12 is a graphic comparison of absorption of two samples containing gold, one sample also containing a palladium/hydrogen gas/glycerol matrix modifier according to the present invention.

FIGS. 10, 11 and 12 illustrate the temperature shifting characteristics of the present invention. The graphs shown in the figures each show two absorption peaks, the later profile (on the right) being the matrix modified sample. For each analyte lead (FIG. 10), thallium (FIG. 11), and gold (FIG. 12), the palladium, hydrogen gas and glycerol matrix modifier increases the vaporization temperatures of the analyte causing it to appear later in the time/temperature scheme (temperature plotted as horizontal lines connected by a slanted line showing the temperature increase). The matrix modifier also may improve the peak size and shape, as illustrated in FIG. 11 for the thallium sample.

Table I, reproduced below, indicates atomic absorption measurement of lead and thallium in varying interferring solutions. Spike recoveries were calculated in both peak height and area, compared to an interferent free standard and modifier absorbance signals. These excellent results were obtained by wall atomization; no platform was used.

TABLE I

INTERFERENCE STUDIES
Pd/glycerol/$H_2$ Matrix Modification

| Interference Solutions | Spike Recoveries | |
|---|---|---|
| | LEAD 1000 C Ash 2600 C Atomize | THALLIUM 900 C Ash 2600 C Atomize |
| 5 uL conc HCl | 98% (Ht) 96% (Area) | 99% (Ht) 101% (Area) |
| 5 uL 5.0% NaCl | 89% 101% | 89% 93% |
| 5 uL sea $H_2O$ | 96% 105% | 103% 100% |
| 5 uL conc $HNO_3$ | 98% 102% | 98% 103% |
| 5 uL 1.0% $Na_2SO_4$ | 89% 95% | 86% 89% |

For purposes of these tests a solution ob 1000–1500 ug/mL palladium containing 1 percent glycerol was introduced into the graphite furnace along with the sample. The solution was dried and 5 percent hydrogen and 95 percent argon was introduced at 3 liters/minute (usually 40 to 60 seconds after the dry phase, during a temperature increase of from 90° C. to 300° C.). Glycerol does not decompose until approximately 290° C., so the reduction of palladium is essentially done after the water has evaporated, above 100° C., and with the glycerol still present. The 5 percent hydrogen can be used during the rest of the temperature program.

The conclusion drawn from the general results of Table I is that the palladium matrix modifier presented in its most efficient form, as taught by the present invention, gives strikingly good results for such items as lead and thallium. The present invention allows palladium to be presented in the graphite furnace to the metal analytes in such an optimum surface such that it can be used as a broadly useable modifier for the transition elements and elements in periodic groups III, IV, V and VI.

Palladium is a very effective chemical modifier for periodic groups III, IV, V and VI, resulting in a several hundred degree higher vaporation temperatures, for example, semi-metallic elements such as arsenic, selenium, tellurium, bismuth, antimony, lead, thallium, gallium, germanium and phosphorus. Ash temperatures can be raised 400° to 800° higher than current methods allow. Temperatures are somewhat less for the transition metals and ash temperatures, ash temperatures being raised only 200° C. to 500° higher than other matrix modifying methods. Preferably, palladium is introduced into the furnace with the sample solution as a chloride or nitrate salt.

The invention contemplates reduction by a reducing gas; about 1 to 10 percent hydrogen gas in about 90–99 percent argon. However, preferably, a 5 percent in 95 percent argon environment is used. It is believed that hydrogen promotes formation of palladium metals earlier in the temperature program, after evaporation of water, but prior to decomposition of added surfactants.

Although glycerol has been used as the surfactant in a large number of tests of the claimed method and in the matrix modifier, it is believed that any surfactant having chemical stability at a temperature at which palladium is reduced in the graphite furnace, or higher, can be used. Other surfactants known to work are polyethylene glycol, Triton-X ® (made by Rohm & Haas) ethylene glycol, polydimethyl siloxane and mixtures thereof. A mixture of polyethlene glycol (PEG) and polydimethyl siloxane is commercially known as Dow antifoam reagent B, made by Dow Chemical Corporation, Midland, Mich.

The relative improvements of the matrix modifier palladium reduced by $H_2$ gas and the modifier palladium with glycerol in solution reduced by hydrogen gas is shown in Table II reproduced below. For the wide range of interfering solutions shown, the palladium/$H_2$ modifier improves over the performance of palladium/ascorbic acid. A slight improvement still is seen for palladium/$H_2$/glycerol as compared to the palladium/$H_2$ alone.

From the above description, it will be apparent that there is provided a matrix modifier and method for modifying a matrix with the advantages mentioned as desirable, but which is clearly susceptible to modification in its form and operation, and in the proportions and arrangement without departing from the principles involved or sacrificing any of its advantages.

It is understood that the invention is not limited to the specific embodiments described but the means, method and construction herein disclosed comprise a preferred form of several modes of putting the invention into effect and the invention is therefore, claimed in any of its forms and modifications within the legitimate and valid scope of the appended claims.

TABLE II

THALLIUM
Spike Recoveries in Interfering Matrices
Palladium Chemical Modification

| Interfering Solution | 20 ug Pd 200 ug Hydrox. HCl | 20 ug Pd 60 ug Ascorbic Acid | 20 ug Pd $H_2$ | 20 ug Pd 100 ug Glycerol $H_2$ |
|---|---|---|---|---|
| 5 uL 2.5% NaCl | 90% (Ht) 96% (Area) | 93% (Ht) 93% (Area) | 95% (Ht) 103% (Area) | 93% (Ht) 96% (Area) |
| 5 uL 5.0% NaCl | 75% 86% | 91% 90% | 75% 84% | 89% 93% |
| 5 uL Sea $H_2O$ | 32% 20% | 87% 69% | 65% 41% | 103% 100% |
| 5 uL conc HCl | 95% 97% | 86% 99% | 101% 87% | 99% 101% |
| 5 uL conc $HNO_3$ | 0 0 | 88% 87% | 103% 101% | 98% 103% |
| 5 uL 20% $H_2SO_4$ | 65% | 85% | 84% | 81% |

TABLE II-continued

THALLIUM
Spike Recoveries in Interfering Matrices
Palladium Chemical Modification

| Interfering Solution | 20 ug Pd 200 ug Hydrox. HCl | 20 ug Pd 60 ug Ascorbic Acid | 20 ug Pd $H_2$ | 20 ug Pd 100 ug Glycerol $H_2$ |
|---|---|---|---|---|
| 5 uL 1.0% $Na_2SO_4$ | 67% 70% 69% | 87% 65% 78% | 61% 75% 65% | 85% 86% 89% |

I claim:

1. In a graphite furnace for vaporization of metallic constituents in a sample during atomic absorption spectroscopic analysis the improvement comprising:
   a) an interior wall surface,
   b) said interior wall surface further comprising finally divided palladium metal particles dispersed thereon over at least a portion of said interior wall surface.

2. The graphite furnace of claim 1 and wherein the improvement further comprising the palladium metal particles have an average diameter no greater than about 10 microns.

3. The graphite furnace of claim 1 and wherein the improvement further comprising said interior wall surface further comprises a sample receiving platform.

* * * * *